(12) United States Patent
Lee et al.

(10) Patent No.: US 8,304,448 B2
(45) Date of Patent: Nov. 6, 2012

(54) METHOD FOR THE TREATMENT OF METABOLIC DISORDER CONTAINING BENZAZOLE DERIVATIVES AS AN ACTIVE INGREDIENT

(75) Inventors: Hyun Sun Lee, Taejeon-si (KR); Kyeong Lee, Taejeon-si (KR); Jung Joon Lee, Taejeon-si (KR); Young Kook Kim, Taejeon-si (KR); Mun-Chual Rho, Taejeon-si (KR); Jeong Hyung Lee, Taejeon-si (KR); Young Soo Hong, Taejeon-si (KR); Hye-Ran Park, Kyeonggi-do (KR); Chul-Ho Lee, Taejeon-si (KR); Yongseok Choi, Seoul (KR)

(73) Assignee: Korea Research Institute of Bioscience and Biotechnology, Daejeon-Si (KR)

( * ) Notice: Subject to any disclaimer, the term of this patent is extended or adjusted under 35 U.S.C. 154(b) by 533 days.

(21) Appl. No.: 12/442,895

(22) PCT Filed: Sep. 27, 2007

(86) PCT No.: PCT/KR2007/004724
§ 371 (c)(1),
(2), (4) Date: Mar. 25, 2009

(87) PCT Pub. No.: WO2008/039008
PCT Pub. Date: Apr. 3, 2008

(65) Prior Publication Data
US 2010/0076039 A1   Mar. 25, 2010

(30) Foreign Application Priority Data
Sep. 27, 2006 (KR) .................. 10-2006-0094131

(51) Int. Cl.
*A61K 31/40* (2006.01)
*A61K 31/405* (2006.01)
(52) U.S. Cl. .................. 514/412; 514/415; 514/909
(58) Field of Classification Search ............... 514/412, 514/415, 909
See application file for complete search history.

(56) References Cited

U.S. PATENT DOCUMENTS

| 5,886,014 A * | 3/1999 | Fujita et al. .................. 514/369 |
| 6,432,682 B1 | 8/2002 | Omura et al. |
| 6,608,185 B1 | 8/2003 | Omura et al. |
| 2003/0069294 A1 | 4/2003 | Fujita et al. |

FOREIGN PATENT DOCUMENTS

| JP | 2004-067629 | 3/2004 |
| KR | 0460438 | 6/2003 |
| KR | 0577320 | 4/2004 |
| KR | 0507989 | 7/2004 |
| WO | WO2006/004200 | 1/2006 |
| WO | WO2006/019020 | 2/2006 |
| WO | WO2006/044775 | 4/2006 |

OTHER PUBLICATIONS

Chen et al. (2002) "Increased insulin and leptin sensitivity in mice lacking acyl CoA:diacylglycerol acyltransferase 1," *J. Clin. Invest.*, 109(8), 1049-1055.
Chen, H.C., et al. (2000) "DGAT and Triglyceride Synthesis: A New Target for Obesity Treatment?" *Trends Cardiovasc. Med.*, 10, 188-192.
Chen et al. (2003) "Obesity resistance and enhanced glucose metabolism in mice transplanted with white adipose tissue lacking acyl CoA:diaclyglycerol acyltransferase," *J. Clin. Invest.*, 111, 1715-1722.
Chen et al. (2003) " Anaysis of energy expenditure at different ambient temperatures in mice lacking DGAT1," *Am. J. Physiol. Endocronol. Metab.*, 284, E213-218.
Chen et al.(2005) "Inhibition of Triglyceride Synthesis as a Treatment Strategy for Obesity: Lessons From DGAT1-Deficient Mice," *Arterioscler Thromb Vasc. Biol.* 25(3), 482-486.
Chen et al. (2002), "Dissociation of Obesity and Impaired Glucose Disposal in Mice Overexpressing Acyl Coenzyme A: Diacylglycerol Acyltransferase 1 in White Adipose Tissue," *Diabetes.* 51(11), 3189-3195.
Ganji et al. (2004) "Niacin noncompetitively inhibits DGAT2 but not DGAT1 activity in HepG2 cells," *Journal of Lipid Research* 45:1835-1845.
Rustan et al. (1988) "Eicosapentaenoic acid reduces hepatic synthesis and secretion of triacyglycerol by decreasing the activity of acyl-coenzyme A:1,2-diacyglycerol acyltransferase," *Journal of Lipid Research* 29:1417-1426.
Smith, S.J. et al.(2000) "Obesity resistance and multiple mechanisms of triglyceride synthesis in mice lacking NAT," *Nature genetics*, 25, 87-90.
Subauste et. al. (2003) "DGAT: Novel Therapeutic Target for Obesity and Type 2 Diabetes Mellitus," *Current Drug Target-Immun2, Endocrine & Metabol Disorders*, 3, 263-270.
Yoganathan et al. (2004) "Cochlioquinones and Epi-Cochlioquinones Antagonists of the Human Chemokine Receptor CCR5 from *Bipolaris brizae* and *Stachybotrys chartarum*," *The Journal of Antibiotics* 57,1:59-63.
International Search Report and Written Opinion dated Nov. 28, 2007 for PCT/KR2007/00724.

* cited by examiner

*Primary Examiner* — Kevin E Weddington
(74) *Attorney, Agent, or Firm* — Greenlee Sullivan P.C.

(57) ABSTRACT

Disclosed is a composition for the prevention and treatment of metabolic diseases, which comprises a benzazole derivative as an active ingredient. The benzazole derivative has inhibitory activity against DGAT (diacylglycerol acyltransferase), which causes metabolic diseases such as obesity and diabetes in the process of lipid metabolism. With the ability to effectively control lipid metabolism and energy metabolism, thus, the composition is useful in the prevention and treatment of metabolic diseases, such as obesity and diabetes.

5 Claims, 4 Drawing Sheets

METHOD FOR THE TREATMENT OF METABOLIC DISORDER CONTAINING BENZAZOLE DERIVATIVES AS AN ACTIVE INGREDIENT

CROSS-REFERENCE TO RELATED APPLICATIONS

This application is the U.S. National Stage of International Application No. PCT/KR2007/004724, filed Sep. 27, 2007, which claims the benefit of Korean Patent Application KR10-2006-0094131, filed Sep. 27, 2006, both of which are hereby incorporated by reference to the extent not inconsistent with the disclosure hereof.

TECHNICAL FIELD

The present invention relates to a composition for the prevention and treatment of metabolic disorders, such as obesity, diabetes and the like, containing, as an active ingredient, a benzazole derivative having high inhibitory activity against diacylglycerol acyltransferase.

BACKGROUND ART

Acyl CoA:diacylglycerol acyltransferase (hereinafter referred to as "DGAT") is an integral membrane enzyme that catalyses the last step of the glycerol 3-phosphate pathway, synthesizing triacylglycerol from the substrates sn-1,2-diacylglycerol and fatty acyl CoA. As a rule, the biosynthesis of triacylglycerol is accomplished through the glycerol 3-monophosphate pathway (the liver and adipose tissues) and the monoacylglycerol pathway (intestinal epithelial cells).

Recently, at the Gladstone Institute of Cardiovascular Diseases, U.S.A., DGAT-1 gene deficient mice have been used in the study of DGAT functions, yielding evidence that DGAT-1 deficient mice are protected from diet-induced obesity even when they are weaned on a high-fat diet, and that DGAT-1 deficiency enhances insulin and leptin deficiency, improving glucose metabolism. A subsequent research result showed that the selective inhibition of DGAT, an enzyme that catalyzes the biosynthesis of triglycerides in insulin-sensitive tissues, such as adipose tissues, skeletal muscles, the liver, beta cells of the pancreas, etc., is useful in the prevention and treatment of obesity and type II diabetes mellitus (Chen H C, et al., *Trends Cardiovasc. Med.*, 10, 188-192, 2000; Farese Jr. et al., *Curr. Opin. Lipidol.*, 11, 229-234, 2000; A. Subauste et. al., *Current Drug Target-Immun, Endocrine & Metabol Disorders*, 3, 263-270, 2003; Y. Yu et. al. *Annals of Medicine*, 36. 252-261).

Decreased activity of DGAT results in the blockage of enzymatic reactions for triglyceride biosynthesis or a reduction in biosynthesis yield. When the biosynthesis of triglyceride is restricted by inhibiting DGAT, an enzyme participating in the final step of triglyceride biosynthesis, there are a decrease in the accumulation of fats in adipose tissues, a decrease in the size of adipose cells, and an increase in energy expenditure attributable to increased ambulatory physical activity and increased expression of uncoupling proteins, thereby giving rise to resistance to diet-induced obesity (Smith S J. et al., *Nature genetics*, 25, 87-90, 2000; Chen et al., *J Clin Invest.*, 109(8), 1049-1055, 2002; Chen et al., *J Clin Invest.*, 111, 1715-1722, 2003; Chen et al. *Am. J. Physiol. Endocronol. Metab.*, 284, E213-218, 2003).

In addition, it is known that the inhibition of DGAT restricts the accumulation of fats in non-adipose tissues, such as the skeletal muscles, the liver, the pancreas and the like, leading to an improvement in insulin resistance.

Insulin stimulation results in decreased serine inhibitory phosphorylation and tyrosine phosphorylation of IRS-1 (insulin receptor substance-1), and increased insulin signaling transduction through PI-3K (phosphatidylinositol-3 kinase), PKB (protein kinase B, Akt) and PKC, (protein kinase $C_\lambda$), thereby increasing the number of the glucose transporter GLUT-4.

When the activity of DGAT within cells is decreased, the activities of PI-3K, PKB and PKC, increase, thus stimulating GLUT-4 exocytosis and increasing the amount of glucose introduced into the cells. In other words, the inhibition of DGAT activity enhances insulin sensitivity (Chen et al., *Arterioscler Thromb Vasc Biol.* 25(3), 482-486, 2005; Chen et al., *J Clin Invest.* 111(11), 1715-22, 2003; Chen et al., *J Clin Invest.* 109(8), 1049-1055, 2002; Chen et al., *Diabetes.* 51(11), 3189-3195, 2002; Subauste and Burant., *Curr Drug Targets Immune Endocr Metabol Disord.* 3(4), 263-270, 2003). With the discovery of the correlation between the inhibition of DGAT and the subjugation of insulin resistance, DGAT arises as a therapeutic target for type II diabetes mellitus, which is characterized by the obstruction of glucose absorption due to insulin resistance, but with normal insulin secretion.

Synthetic chemicals known as DGAT inhibitors include biphenyl-4-yl-carbonylaminoacid derivatives (WO2006044775, Bayer Pharmaceuticals Corp), urea derivatives (WO2006019020, WO2006004200, Sankyo Co), pyrrolecarboxylic acid derivatives (JP05213985A, Mitsubishi Kasei Corp, Japan) and phosphonic acid ester derivatives (JP2004067635A, Otsuka Pharmaceut Factory Inc., Japan). DGAT inhibitors in the foam of naturally occurring materials include polyacetylenes from Ginseng (Korean Patent No. 0460438, Lee et al. *Planta Med.* 70, 179-200, 2004), quinolone alkaloids, tanshinones, prenyl flavonoids isolated from *Evodia officinalis, Salvia miltiorrhiza* BUNGE, and *Sophora flavescens* (Korean Pat. No. 0577320, Ko et al., *Arch. Phar. Res.* 25, 446-448, 2002, Korean Patent No. 0507989).

Also reported as DGAT inhibitors are roselipins (U.S. Pat. Nos. 6,432,682 (2002) and 6,608,185 (2003)) (Omura et al., the Kitasato Institute and Graduate School of Pharmaceutical Sciences), cochlioquinone A and A1 (*J. Antibiot.*, 56, 967, 2003; *J. Antibiot.*, 57, 59, 2004), amidepsines and xanthohumol. Other examples include eicosapentaenoic acid, 2-bromooctanoate and niacin (Rustan et al., *J. Lipid. Res.*, 29, 1417-1426, 1988, Ganji et al. *J. Lipid. Res.*, 45, 1835-1845).

Leading to the present invention, intensive and thorough research into active materials inhibitory of DGAT, conducted by the present inventors, resulted in the finding that benzazole derivatives inhibit the biosynthesis of triglycerides to bring about various effects including the prevention of diet-induced obesity, the amelioration of blood lipid levels, and the prevention of fat accumulation in adipose cells, and thus can be applied to the treatment of metabolic disorders, such as obesity, diabetes and the like.

DISCLOSURE

Technical Problem

It is an object of the present invention to provide a composition for the prevention and treatment of metabolic disorders, comprising a benzazole derivative or a pharmaceutically acceptable salt thereof as an active ingredient.

Technical Solution

In order to accomplish the above object, the present invention provides a composition for the prevention and treatment of metabolic disorders, comprising a benzazole derivative or a pharmaceutically acceptable salt thereof as an active ingredient.

Advantageous Effects

The benzazole derivatives according to the present invention effectively inhibit diacylglycerol acyltransferase (DGAT), an enzyme which may cause metabolic disorders, such as obesity and diabetes, in the process of lipid metabolism, and thus can be used as a therapeutic for the treatment of metabolic disorders, such as obesity and diabetes.

BEST MODE

In accordance with an aspect thereof, the present invention provides a composition for the prevention and treatment of metabolic disorders, comprising a benzazole derivative, represented by the following Chemical Formula 1, or a pharmaceutically acceptable salt thereof as an active ingredient.

[Chemical Formula 1]

wherein,
$R_1$ is one substituent at position C5 or C6 of a benzoxazole or benzimidazole ring, which is selected from a group consisting of H, $COOR_a$, $CONR_bR_c$ and $SO_2NH_2$
  wherein $R_a$ is H or a $C_1$~$C_2$ alkyl group, and
  $R_b$ and $R_c$ are independently selected from a group consisting of: a $C_3$~$C_5$ heteroaryl group bearing at least one heteroatom selected from among N, O and S; a $C_3$~$C_5$ heterocyclic group bearing at least one heteroatom selected from among N, O and S; a $C_1$~$C_5$ alkyl group bearing a $C_1$~$C_3$ alkyl-substituted amino group; H; an amino group; and a $C_1$~$C_3$ alkyl group; group;
  $R_2$ is a $C_1$~$C_{10}$ alkyl group, a halogen atom or a nitro
  $R_3$ is H or a halogen atom; and
  X is O or NH.

Concrete examples of the derivatives of Chemical Formula 1 useful as an active ingredient of the composition for the prevention and treatment of metabolic disorders, such as obesity and diabetes, include:

1) 2-(2,4-dichloro-phenoxymethyl)-benzoxazole-5-carboxylic acid methyl ester;
2) 2-(4-adamantan-1-yl-phenoxymethyl)-benzoxazole-5-carboxylic acid methyl ester;
3) 2-(4-adamantan-1-yl-phenoxymethyl)-benzoxazole-6-carboxylic acid methyl ester;
4) 2-(4-adamantan-1-yl-phenoxymethyl)-1H-benzoimidazole-5-carboxylic acid methyl ester;
5) 2-(2,4-dichloro-phenoxymethyl)-benzoxazole-6-carboxylic acid methyl ester;
6) 2-(2,4-dichloro-phenoxymethyl)-1H-benzoimidazole-5-carboxylic acid methyl ester;
7) 2-(2,4-tert-butyl-phenoxymethyl)-benzoxazole-6-carboxylic acid methyl ester;
8) 2-(2,4-tert-butyl-phenoxymethyl)-1H-benzoimidazole-5-carboxylic acid methyl ester;
9) 2-(4-nitro-phenoxymethyl)-1H-benzoimidazole-5-carboxylic acid methyl ester;
10) 2-(2,4-dichloro-phenoxymethyl)-benzoxazole-5-sulfonic acid amide;
11) 2-(2,4-dichloro-phenoxymethyl)-benzoxazole-5-carboxylic acid;
12) 2-(4-adamantan-1-yl-phenoxymethyl)-benzoxazole-5-carboxylic acid;
13) 2-(4-adamantan-1-yl-phenoxymethyl)-benzoxazole-6-carboxylic acid;
14) 2-(4-adamantan-1-yl-phenoxymethyl)-1H-benzoimidazole-5-carboxylic acid;
15) 2-(2,4-dichloro-phenoxymethyl)-benzoxazole-6-carboxylic acid;
16) 2-(2,4-dichloro-phenoxymethyl)-1H-benzoimidazole-5-carboxylic acid;
17) 2-(4-tert-butyl-phenoxymethyl)-benzoxazole-6-carboxylic acid;
18) 2-(4-tert-butyl-phenoxymethyl)-1H-benzoimidazole-5-carboxylic acid;
19) 2-(4-nitro-phenoxymethyl)-1H-benzoimidazole-5-carboxylic acid;
20) 2-(4-adamantan-1-yl-phenoxymethyl)-benzoxazole-5-carboxylic acid amide;
21) 2-(4-adamantan-1-yl-phenoxymethyl)-benzoxazole-5-carboxylic acid dimethylamide;
22) 2-(4-adamantan-1-yl-phenoxymethyl)-benzoxazole-5-carboxylic acid (furan-2-ylmethyl)-amide;
23) 2-(4-adamantan-1-yl-phenoxymethyl)-benzoxazole-5-carboxylic acid (2-dimethylamino-ethyl)-amide;
24) 2-(4-adamantan-1-yl-phenoxymethyl)-benzoxazole-5-carboxylic acid (2-piperidin-1-yl-ethyl)-amide;
25) 2-(4-adamantan-1-yl-phenoxymethyl)-benzoxazole-5-carboxylic acid (3-morpholin-4-yl-propyl)-amide;
26) 2-(2,4-dichloro-phenoxymethyl)-benzoxazole-5-carboxylic acid (furan-2-ylmethyl)-amide;
27) 2-(4-adamantan-1-yl-phenoxymethyl)-benzoxazole-6-carboxylic acid (furan-2-ylmethyl-amide;
28) 2-(2,4-dichloro-phenoxymethyl)-benzoxazole-6-carboxylic acid (furan-2-ylmethyl)-amide;

29) 2-(4-adamantan-1-yl-phenoxymethyl)-3H-benzoimidazole-5-carboxylic acid amide;
30) 2-(4-adamantan-1-yl-phenoxymethyl)-3H-benzoimidazole-5-carboxylic acid dimethylamide;
31) 2-(4-adamantan-1-yl-phenoxymethyl)-1H-benzoimidazole-5-carboxylic acid (furan-2-ylmethyl)-amide;
32) 2-(4-adamantan-1-yl-phenoxymethyl)-1H-benzoimidazole-5-carboxylic acid (2-dimethylamino-ethyl)-amide;
33) 2-(4-adamantan-1-yl-phenoxymethyl)-1H-benzoimidazole-5-carboxylic acid (3-imidazol-1-yl-propyl)-amide;
34) 2-(2,4-dichloro-phenoxymethyl)-1H-benzoimidazole-5-carboxylic acid hydrazide; and
35) 2-(2,4-dichloro-phenoxymethyl)-3H-benzoimidazole-5-carboxylic acid (furan-2-ylmethyl)-amide.

The derivatives of Chemical Formula 1 are summarized with regard to structure, $R_1$, $R_2$, $R_3$ and X in Table 1, below.

TABLE 1

| Cpd. | $R_1$ ($C_5$-position) | $R_1$ ($C_6$-position) | $R_2$ | $R_3$ | X |
|---|---|---|---|---|---|
| 1 | COOCH₃ | H | Cl | Cl | O |
| 2 | COOCH₃ | H | adamantyl | H | O |
| 3 | H | COOCH₃ | adamantyl | H | O |
| 4 | H | COOCH₃ | adamantyl | H | NH |
| 5 | H | COOCH₃ | Cl | Cl | O |
| 6 | H | COOCH₃ | Cl | Cl | NH |
| 7 | H | COOCH₃ | tert-butyl | H | O |
| 8 | H | COOCH₃ | tert-butyl | H | NH |
| 9 | H | COOCH₃ | NO₂ | H | NH |
| 10 | H₂N-SO₂- | H | Cl | Cl | O |
| 11 | COOH | H | Cl | Cl | O |
| 12 | COOH | H | adamantyl | H | O |

TABLE 1-continued

| Cpd. | R₁ (C₅-position) | R₁ (C₆-position) | R₂ | R₃ | X |
|---|---|---|---|---|---|
| 13 | H | COOH | adamantyl | H | O |
| 14 | H | COOH | adamantyl | H | NH |
| 15 | H | COOH | Cl | Cl | O |
| 16 | H | COOH | Cl | Cl | NH |
| 17 | H | COOH | tert-butyl | H | O |
| 18 | H | COOH | tert-butyl | H | NH |
| 19 | H | COOH | NO₂ | H | NH |
| 20 | CONH₂ | H | adamantyl | H | O |
| 21 | -C(O)N(CH₃)₂ | H | adamantyl | H | O |
| 22 | furfuryl-NH-C(O)- | H | adamantyl | H | O |
| 23 | (CH₃)₂N-CH₂CH₂-NH-C(O)- | H | adamantyl | H | O |
| 24 | piperidinyl-CH₂CH₂-NH-C(O)- | H | adamantyl | H | O |

TABLE 1-continued

| Cpd. | R$_1$ (C$_5$-position) | R$_1$ (C$_6$-position) | R$_2$ | R$_3$ | X |
|---|---|---|---|---|---|
| 25 |  | H |  | H | O |
| 26 |  | H |  | Cl | O |
| 27 | H |  |  | H | O |
| 28 | H |  |  | Cl | O |
| 29 | H | CONH$_2$ |  | H | NH |
| 30 | H |  |  | H | NH |

TABLE 1-continued

| Cpd. | R₁ (C₅-position) | R₁ (C₆-position) | R₂ | R₃ | X |
|---|---|---|---|---|---|
| 31 | H | furfurylmethyl-NHC(O)- | adamantyl | H | NH |
| 32 | H | (CH₃)₂NCH₂CH₂NHC(O)- | adamantyl | H | NH |
| 33 | H | imidazolyl-propyl-NHC(O)- | adamantyl | H | NH |
| 34 | H | CONHNH₂ | Cl | Cl | NH |
| 35 | H | furfurylmethyl-NHC(O)- | Cl | Cl | NH |

Also, the benzazole derivatives represented by Chemical Formula 1 may be used in the form of pharmaceutically acceptable salts. The pharmaceutical acceptable salts useful in the present invention may be addition salts of acceptable free acids. Organic or inorganic acids may be used for the formation of acid addition salts. Suitable as inorganic acids are hydrochloric acid, bromic acid, sulfuric acid and phosphoric acid. Examples of suitable organic acids include citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid, and aspartic acid.

Furthermore, the present invention includes the hydrates and solvates of the benzazole derivatives of Chemical Formula 1, and salts thereof.

The benzazole derivatives of Chemical Formula 1 for use in the prevention and treatment of metabolic disorders may be synthesized as elucidated in Reaction Scheme 1, below. A general description is given of the synthesis of the benzazole derivatives, below. In Reaction Scheme 1, Compounds 1a, 1b and 1c correspond to the derivatives of Chemical Formula 1.

[Reaction Scheme 1]

(wherein, $R_1$, $R_2$, $R_3$ and X are as defined in Chemical Formula 1)

Phenoxy acetic acid 3, which is commercially available or can be easily prepared by well-known methods, is condensed with an ester 3, synthesized by a well-known method, at an equivalent ratio in the presence of triethylsilyl polyphosphate for 2-4 hours at 140~160° C. to produce Compound 1a.

When $R_1$ is $COOR_a$, the following Reaction Scheme 2 may be further performed.

[Reaction Scheme 2]

(wherein, $R_2$, $R_3$, $R_a$, $R_b$, $R_c$ and X are as defined in Chemical Formula 1)

In greater detail,

1) The ester compound 1a is reacted with aluminum bromide in the presence of dimethylsulfide in methylene chloride at room temperature for 2~3 hours to produce a carboxy compound 1b. Alternatively, the ester compound 1a can be refluxed in the presence of an acid to give carboxy compound 1b.

2) The ester compound 1a or the carboxylic acid compound 1b can be used to synthesize a corresponding amide compound 1c. In this regard, first, a commercially available alkyl amine is stirred at room temperature for 30 min in the presence of triethyl aluminum (2M hexane solution) in anhydrous toluene. To the resulting mixture was added a solution of compound 1a in toluene, followed by fluxing at 80° C. for 1~2 hours to synthesize amide compound 1c. Alternatively, the production of the amide compound 1b can be realized by reacting the carboxylic acid compound 1b with a compound selected from among ammonium chloride, hydrazine hydrate and alkyl amine with the aid of a condensing reagent in the presence of a base in dimethylformamide (DMF) at room temperature. The condensing reagent is selected from among ethylene dichloride (EDC), N-hydroxy benzotriazole (HOBt), O-(benzotriazol-1-yl)-1,1,3,3-tetramethyluronium hexafluorophosphate (HBTU), O-(7-azabenzotriazol-1-yl)-N,N,N',N'-tetramethyluronium hexafluorophosphate (HATU) and combinations thereof while N,N-diisopropylethylamine is used as the base.

The following explanation is given with regard to the use of the derivatives of Chemical Formula 1 or pharmaceutically acceptable salts thereof.

In accordance with an aspect thereof, the present invention provides a composition for the prevention and treatment of metabolic diseases, comprising a benzazole derivative represented by Chemical Formula 1 or a pharmaceutically acceptable salt thereof as an active ingredient.

In an embodiment of the aspect, the present invention provides a composition useful in the prevention and treatment of obesity.

In another embodiment, the present invention provides a composition useful in the prevention and treatment of diabetes mellitus.

In a further embodiment, the present invention provides a composition useful in the prevention and treatment of hyperlipidemia.

In still a further embodiment, the present invention provides a composition useful in the prevention and treatment of arteriosclerosis.

In accordance with another aspect thereof, the present invention provides a DGAT inhibitor comprising a benzazole derivative, represented by Chemical Formula 1 or a pharmaceutically acceptable salt thereof, as an active ingredient.

In accordance with a further aspect thereof, the present invention provides a triglyceride production inhibitor comprising a benzazole derivative, represented by Chemical Formula 1 or a pharmaceutically acceptable salt thereof, as an active ingredient.

DGAT is an integral membrane enzyme that catalyses the last step of the glycerol 3-phosphate pathway to synthesize triacylglycerides using sn-1,2-diacylglycerol and fatty acyl CoA as substrates. Generally, triglyceride biosynthesis follows the glycerol 3-monophosphate pathway (the liver and adipose tissues) and the monoacylglycerol pathway (intestinal epithelial cells).

It is reported that the inhibition of triglyceride biosynthesis results in the suppression of fat accumulation in adipose tissues, a decrease in the size of adipose cells, the stimulation of adiponectin secretion from adipose cells, an increase in ambulatory physical activity, and resistance to diet-induced obesity (Smith S J. et al., Nature genetics, 25, 87-90, 2000; Chen et al., J Clin Invest., 109(8), 1049-1055, 2002; Chen et al., J Clin Invest., 111, 1715-1722, 2003; Chen et al. Am. J. Physiol. Endocrinol. Metab., 284, E213-218, 2003).

Also, DGAT inhibition is known to suppress the accumulation of fats in non-adipose tissues, such as the skeletal muscles, the liver, the pancreas and the like, thereby giving rise to an improvement in insulin resistance.

Upon insulin stimulation, the serine inhibitory phosphorylation of IRS-1 (insulin receptor substance-1) decreases with an increase in the activity of insulin signal transduction through PI-3K (phosphatidylinositol-3 kinase), PKB (protein kinase B, Akt) and PKC, (protein kinase $C_\lambda$), to stimulate GLUT-4 (glucose transporter-4) exocytosis and thus stimulate the introduction of glucose into cells.

In other words, the inhibition of DGAT activity enhances insulin sensitivity to thus improve insulin resistance (Chen et al., Arterioscler Thromb Vasc Biol. 25(3): 482-486, 2005; Chen et al., J Clin Invest. 111(11): 1715-22, 2003; Chen et al., J Clin Invest. 109(8): 1049-1055, 2002; Chen et al., Diabetes. 51(11): 3189-3195, 2002; Subauste and Burant., Curr Drug Targets Immune Endocr Metabol Disord. 3(4): 263-270, 2003).

Accordingly, DGAT inhibitors are applicable to the prevention and treatment of metabolic disorders, such as obesity and diabetes. There are many research results reported to act as DGAT inhibitors (Chen H C, et al., Trends Cardiovasc. Med., 10, 188-192, 2000; Farese Jr. et al., Curr. Opin. Lipidol., 11, 229-234, 2000; A. Subauste et. al., Current Drug Target-Immun, Endocrine & Metabol Disorders, 3, 263-270, 2003; Y. Yu et. al. Annals of Medicine, 36. 252-261; Hubert C. et al., Arterioscler. Thromb. Vasc. Biol., 25, 1-5, 2005; Smith J. et al., Nature genetics, 25, 87-90, 2000).

The derivatives of Chemical Formula 1 in accordance with the present invention are found to inhibit the enzymatic activity of DGAT at a dose-dependent manner (refer to Table 2 and FIG. 1) as measured in a test in which [$^{14}$C]triacylglycerol was quantitatively analyzed after enzymatic reaction between 1,2-diacylglycerol and [$^{14}$C]palmitoyl-CoA, with microsomal proteins from rats serving as an enzyme source (refer to Example 1).

In addition, the derivatives of Chemical Formula 1 were found to highly inhibit the biosynthesis of triglyceride (refer to Table 3) as analyzed in a test where the derivatives of Chemical Formula 1 were measured for inhibitory activity against DGAT after the treatment of HepG2 with 10 µM of each of the derivatives (refer to Example 2).

Also, the derivatives of Chemical Formula 1 were tested for resistance to obesity by iterative oral administration at a dose of 10 mg/kg into ICR male mice (refer to Example 3). Derivatives 22 and 31 in accordance with the present invention are highly useful in realizing weight loss as they were found to inhibit weight gain by 68% and 73%, respectively (refer to Table 5 and FIG. 2). When they were administered, the levels of total triglycerides, total cholesterols, and low density lipoprotein (LDL)-cholesterol in the blood recovered to almost normal levels, with a significant increase observed in the level of high density lipoprotein (HDL)-cholesterol in the blood (refer to Tables 6 and 7 and FIGS. 3 and 4). Also, the administration of the derivatives according to the present invention was observed to result in a significant decrease in total fat, abdominal fat, epididymal fat and retroperitoneal fat.

Demonstrated to have potent inhibitory activity against DGAT in vitro and on triglyceride biosynthesis in vivo and induce superior effects of providing weight loss, normalizing blood lipid levels and inhibiting fat accumulation in adipose cells, as analyzed in fat-fed animal models, the composition comprising a derivative of Chemical Formula 1 or a pharmaceutically acceptable salt thereof as an active ingredient can be applied to the prevention and treatment of metabolic disorders, including hyperlipidemia and arteriosclerosis, as well as obesity and diabetes (particularly, type II diabetes mellitus).

The benzazole derivatives of Chemical Formula 1 in accordance with the present invention can be administered either orally or non-orally, and may be provided in general medicine forms. For clinical practice, the compounds of the present invention may be used in oral or non-oral forms. It is usually formulated in combination with a diluent or excipient, such as a filler, a thickening agent, a binder, a wetting agent, a disintegrant, a surfactant, etc. Solid agents intended for oral administration of the compound of the present invention may be in the form of tablets, pills, powders, granules, capsules, and the like. These solid agents are formulated in combination with at least one excipient, such as starch, calcium carbonate, sucrose, lactose, or gelatine. Besides, a lubricant, such as magnesium stearate, talc and the like, may also be added. Liquid agents intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid agents for the oral administration of the compound of the present invention. Also, non-oral dosage forms of the compound of the present invention include injections, emulsions, inhalations, and suppositories. For injections, non-aqueous solvents and suspensions made from propylene glycol, polyethylene glycol, vegetable oils such as olive oil, and esters such as ethyl oleate may be used. The basic materials of suppositories include witepsol, macrogol, Tween 61, cacao paper, laurin paper, glycerol, and gelatine.

The benzazole derivatives of Chemical Formula 1 in accordance with the present invention may be administered in a single dose or in two or three doses per day, each dose ranging from 1~250 mg/kg.

MODE FOR INVENTION

A better understanding of the present invention may be obtained in light of the following examples which are set forth to illustrate, but are not to be construed to limit the present invention.

Example 1

Assay for Inhibitory Activity against DGAT

The following experiment was performed in order to examine the inhibitory activity of the benzazole derivatives of Chemical Formula 1 against DGAT.

After enzymatic reaction between two substrates 1,2-diacylglycerol (Sigma, D0138) and [$^{14}$C]palmitoyl-CoA (Amersham, CFA583) with the microsomal protein of rat serving as an enzyme source in accordance with Coleman et al, Methods Enzymol., 98-103, 1992, the resulting product [$^{14}$C] triacylglycerol was measured for radioactivity. In detail, to a reaction buffer (175 mM Tris-HCl, pH 8.0, 20 µl bovine serum albumin (10 mg/ml), 100 mM $MgCl_2$, 30 µM [$^{14}$C] palmitoyl-CoA (0.02 µCi, Amersham) and 200 µM 1,2-dioleoyl glycerol) was added 10 µl of a solution of the samples in dimethylsulfoxide (DMSO) and then 100~200 µl of an isolated microsomal protein, followed by reaction at 25° C. for 10 min. The reaction was terminated with 1.5 ml of a mixture of 80:20:2 2-propanol:heptane:water (v:v:v). Thereafter, the [$^{14}$C] triacylglycerol thus formed was separated. In this regard, 1 ml of heptane and 0.5 ml of distilled water were added to the reaction mixture, which was then shaken. 1 ml of the supernatant thus formed was mixed with 2 ml of an alkaline ethanol solution (ethanol:0.5 N sodium hydroxide:water=50:10:40, v:v:v), followed by shaking. After being taken, 0.65 ml of the supernatant thus formed was measured for radioactivity using an LSC (liquid scintillation counter). The inhibitory activity against DGAT was calculated according to the following Mathematical Formula 1. The inhibitory effects of the benzazole derivatives on DGAT are summarized in Table 2, below while % DGAT inhibition is plotted against doses of compound 22 and 31 in FIG. 1.

$$\% \text{ Inhibition} = \left(1 - \frac{T-B}{C-B}\right) \times 100 \quad \text{[Mathematical Formula 1]}$$

T: Cpm of a test group in which a sample was added to an enzymatic buffer,

C: Cpm of a control in which no samples were added to an enzymatic buffer,

B: Cpm of a control in which a sample was added in the absence of any enzyme source.

TABLE 2

| Cpd. | DGAT (% inhibition in 5 μM) | DGAT (% inhibition in 25 μM) |
|---|---|---|
| 1 | — | −2.64 |
| 2 | — | −25.72 |
| 3 | — | −5.34 |
| 4 | — | 60.43 |
| 5 | — | 1.98 |
| 6 | — | 0.63 |
| 7 | — | 34.5 |
| 8 | — | 37.36 |
| 9 | −5.6 | 0.61 |
| 10 | — | 17.43 |
| 11 | — | −16.48 |
| 12 | — | −10.43 |
| 13 | — | −18.53 |
| 14 | — | −13.17 |
| 15 | — | −13.03 |
| 16 | — | −7.37 |
| 17 | — | −29.81 |
| 18 | — | −13.05 |
| 19 | 2.0 | −5.86 |
| 20 | — | — |
| 21 | — | 10.49 |
| 22 | 42.8 | 78.03 |
| 23 | — | 8.59 |
| 24 | — | 52.84 |
| 25 | — | 54.08 |
| 26 | — | 19.75 |
| 27 | — | 13.26 |
| 28 | — | −8.07 |
| 29 | −1.8 | −13.38 |
| 30 | 8.0 | 41.8 |
| 31 | 62.5 | 85.4 |
| 32 | — | −3.08 |
| 33 | — | 16.99 |
| 34 | — | 6.74 |
| 35 | — | 28.63 |

As shown in Table 2, the compounds of Chemical Formula 1 were found to exert more potent inhibitory activity against DGAT when they were used at higher doses in the presence of rat hepatic microsomal protein as an enzyme source with 1,2-diacylglycerol and [$^{14}$C] palmitoyl-CoA serving as substrates.

Figure 1:
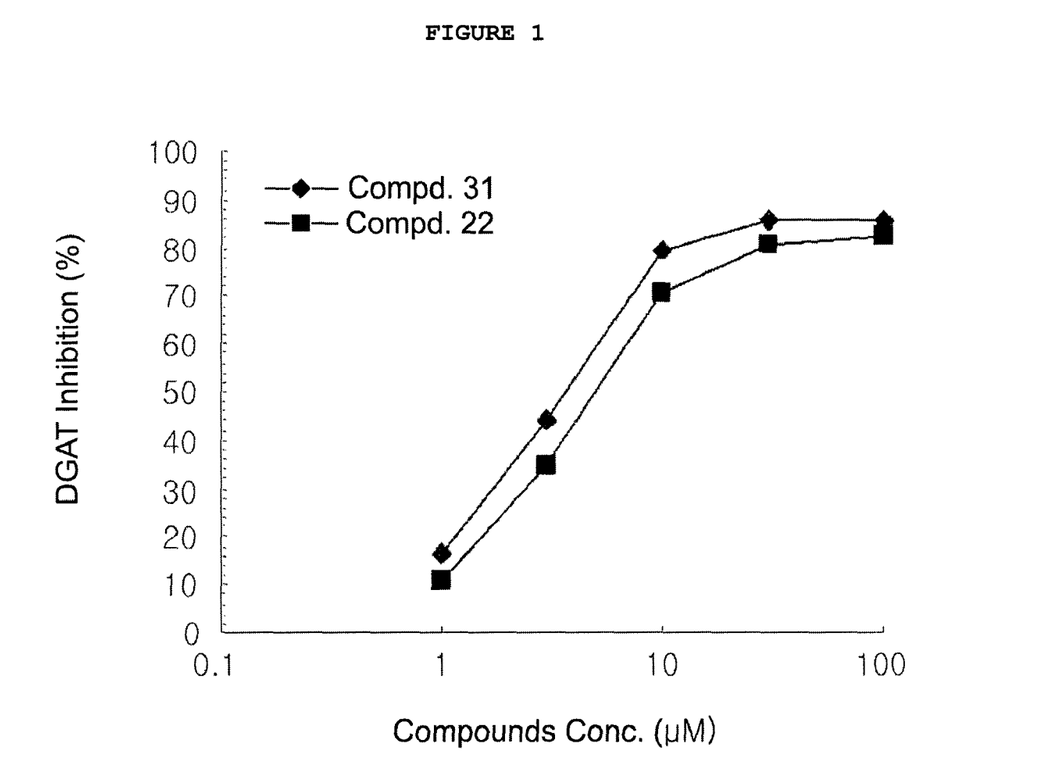
FIG. 1 is a graph in which the inhibitory activity of the benzazole derivatives of Chemical Formula 1 against DGAT is plotted against doses thereof.

As can be understood from the plot of FIG. 1, the DGAT inhibition activity of compounds of Chemical Formula 1 in accordance with the present invention increases in a dose-dependent manner.

Example 2

Assay for Inhibitory Effect on DGAT in Cell

The effect of the benzazole derivatives of Chemical Formula 1 in accordance with the present invention on DGAT was examined with HepG2 cells, hepatic cells derived from the human liver, as follows.

HepG2 cells, purchased from ATCC, were cultured in Eagle's minimum essential medium (MEM), 2 mM L-glutamine, with Earle's balanced salt solution (BSS) adjusted to contain, 1.5 g/L sodium bicarbonate, 0.1 mM non-essential amino acids and 1 mM sodium pyruvate, supplemented with 10% fetal bovine serum (FBS) and 1% antibiotics (100 U/ml penicillin and 100 g/ml streptomycin) at 37° C. in a 5% $CO_2$ incubator.

Intracellular DGAT activity was represented by the amount of triglycerides produced in the cultured HepG2 cells while the compounds (4, 8, 10, 22, 24, 25, 26, 39 and 31) of Chemical Formula 1 were assayed for inhibitory activity against DGAT by measuring the change in intracellular triglyceride production after the addition thereof.

Cells were plated at a density of $1 \times 10^6$ cell/ml per well into 24-well plates and incubated for 24 hours. Then, the medium was exchanged with FBS-free MEM and pre-treated with samples for 1 hour. Thereafter, 0.2 mCi of [$^{14}$C]acetate (Amersham) was added as a substrate to the cells, followed by incubation for 1 hour. The production of triglyceride was catalyzed by DGAT so that DGAT activity was determined by the amount of the triglyceride product, which could be measured by radioactivity. For use, the samples were dissolved in dimethyl sulfoxide (DMSO). In a control, triglycerides were synthesized using DMSO without any sample, with the production yield thereof given as 100.

The amount of the glyceride products synthesized was determined as follows. After completion of synthesis, the cells were suspended in PBS (phosphate-buffer-saline) to remove the substrate [$^{14}$C]acetate, whether unabsorbed into the cells or remaining unreacted, and total lipids, including triglycerides, were extracted twice for 30 min with 0.5 ml of an extraction solvent mixture (hexane:isopropanol=3:2, v:v). 1 ml of the extract was concentrated with nitrogen gas.

The total lipid residue thus formed was dissolved in an organic solvent mixture (chloroform:methanol=2:1) and loaded dropwise onto a thin layer chromatography plate (TLC; silica gel 60F254, 0.5 mm, Merck) using a mixture of 80:20:1 hexane:diethylether:acetic acid (v:v:v) as a developing solvent. After the separation of triglycerides (Rf value: 0.4) on TLC, the plate was brought into contact with an autoradiographic film for three hours, followed by image analysis (BAS-1500, Fuji Photo Film Co. Ltd.) to determine the [$^{14}$C] radioactivity of the triglycerides. The cells left after the extraction were suspended in 0.3 ml of a 0.1 N sodium hydroxide solution to measure the cellular protein concentration thereof.

The empirical values were obtained by dividing triglyceride radioactivity by protein level, with correction for experimental errors between test groups. The inhibitory activities of the compounds according to the present invention against DGAT in vivo are summarized in Table 3, below.

TABLE 3

| Cpd. (Final level 10 μM) | Production Yield of Triglyceride (%) |
|---|---|
| Cpd. 4 | 72.2 ± 7.5 |
| Cpd. 8 | 88.5 ± 5.8 |
| Cpd. 10 | 98.7 ± 6.3 |
| Cpd. 22 | 67.8 ± 7.2 |
| Cpd. 24 | 78.5 ± 6.2 |
| Cpd. 25 | 80.2 ± 7.8 |
| Cpd. 26 | 91.5 ± 5.2 |
| Cpd. 30 | 87.2 ± 7.4 |
| Cpd. 31 | 57.8 ± 5.3 |

As apparent from the data of Table 3, the HepG2 cells treated with 10 μM compounds produced far smaller amounts of triglycerides than did the control. Particularly, Compounds 22 and 31 were measured to inhibit the biosynthesis of triglycerides by 32.2% and 42.2%, respectively. It is also speculated that the inhibition of these compounds occurs within the cells as they enter the cells.

Example 3

In Vivo Assay for Anti-Obesity Activity in Mice

In order to verify the anti-obesity activity of the benzaldehyde derivatives of Chemical Formula 1 in accordance with the present invention, Compounds 22 and 31 were administered repetitively into rodents as follows.

The experimental animals were 6 week old ICR mice which were purchased from Japan SLC, Inc. via Central Lab. Animal Inc. Korea. They were acclimated to a new environment for one week before use, and fed with a foodstuff commercially available from Deyts, U.S.A. They were bred in an animal lab set at a temperature of 23±3° C. and RH 50±10% under light of 150~300 Lux for a period of 12 hours (6 a.m.~6 p.m.) with ventilation 10-20 times/hour. All of the 12 mice used were male, and were organized into two groups of 6. The test group was orally administered once a day at 4 p.m. with 10 mg/kg of the compound (Chemical Formula 1) in the form of a solution in biological saline for 35 days while the control was administered with biological saline only. Xenical, a commercially available lipase inhibitor, was administered orally at a dose of 10 mg/kg once a day as a positive control drug. The mice were fed a normal diet or a high-fat diet, having the compositions shown in Table 4, below.

TABLE 4

| Composition | Normal Diet (g/kg) | High-Fat Diet (g/kg) |
|---|---|---|
| Casein | 200 | 200 |
| Corn Starch | 450 | 200 |
| Cellulose | 50 | 50 |
| Mineral Mix | 35 | 35 |
| Vitamin Mix | 10 | 10 |
| Choline Tartrate | 2 | 2 |
| Methionine | 3 | 3 |
| Sucrose | 200 | 200 |
| Tallow | 13 | 250 |
| Corn Oil | 50 | 50 |
| Cholesterol | — | — |
| Choline chloride | — | — |

The animals were measured for body weight every week and sacrificed on Day 35, after which blood from the heart was sampled. Abdominal fat, epididymal fat, retroperitoneal fat and the liver were excised and weighed. Blood samples were assayed for total triglyceride, total cholesterol, HDL-cholesterol and LDL-cholesterol using respective test kits, all commercially available from Asan Pharmaceutical Co. Ltd., Korea.

For evidence of anti-obesity activity, compounds 22 and 31 were orally administered at regular intervals at a dose of 10 mg/kg into ICR male mice for a predetermined period of time with the concurrent provision of conditional diets thereto. Their body weights were monitored for the time period, and are summarized in Table 5, below. Anatomized abdomens of the animals are given in the photographs of FIG. 2.

TABLE 5

| Groups/Diet | Body Weight (g) (Mean ± SD) | | | | | |
|---|---|---|---|---|---|---|
| | Week 0 | Week 1 | Week 2 | Week 3 | Week 4 | Week 5 |
| Normal Diet | 26.34 ± 1.08 | 32.18 ± 1.77 | 36.31 ± 3.83 | 36.58 ± 3.41 | 39.07 ± 3.17 | 39.69 ± 1.20 |
| High-Fat Diet | 25.29 ± 1.09 | 35.24 ± 1.57 | 37.80 ± 3.55 | 45.90 ± 2.29 | 49.85 ± 1.24 | 52.92 ± 1.20 |
| High-Fat Diet + Cpd. 22 | 26.30 ± 1.27 | 34.75 ± 1.75 | 37.94 ± 2.33 | 40.34 ± 3.39 | 42.48 ± 2.90 | 43.90 ± 1.20 |
| High-Fat Diet + Cpd. 31 | 25.08 ± 0.99 | 35.1 ± 1.99 | 38.93 ± 2.33 | 40.75 ± 1.75 | 42.31 ± 1.57 | 43.22 ± 1.41 |
| High-Fat Diet + Xenical | 26.30 ± 1.45 | 33.63 ± 1.28 | 37.41 ± 2.02 | 39.11 ± 0.90 | 39.95 ± 1.26 | 41.24 ± 1.60 |

Figure 2:
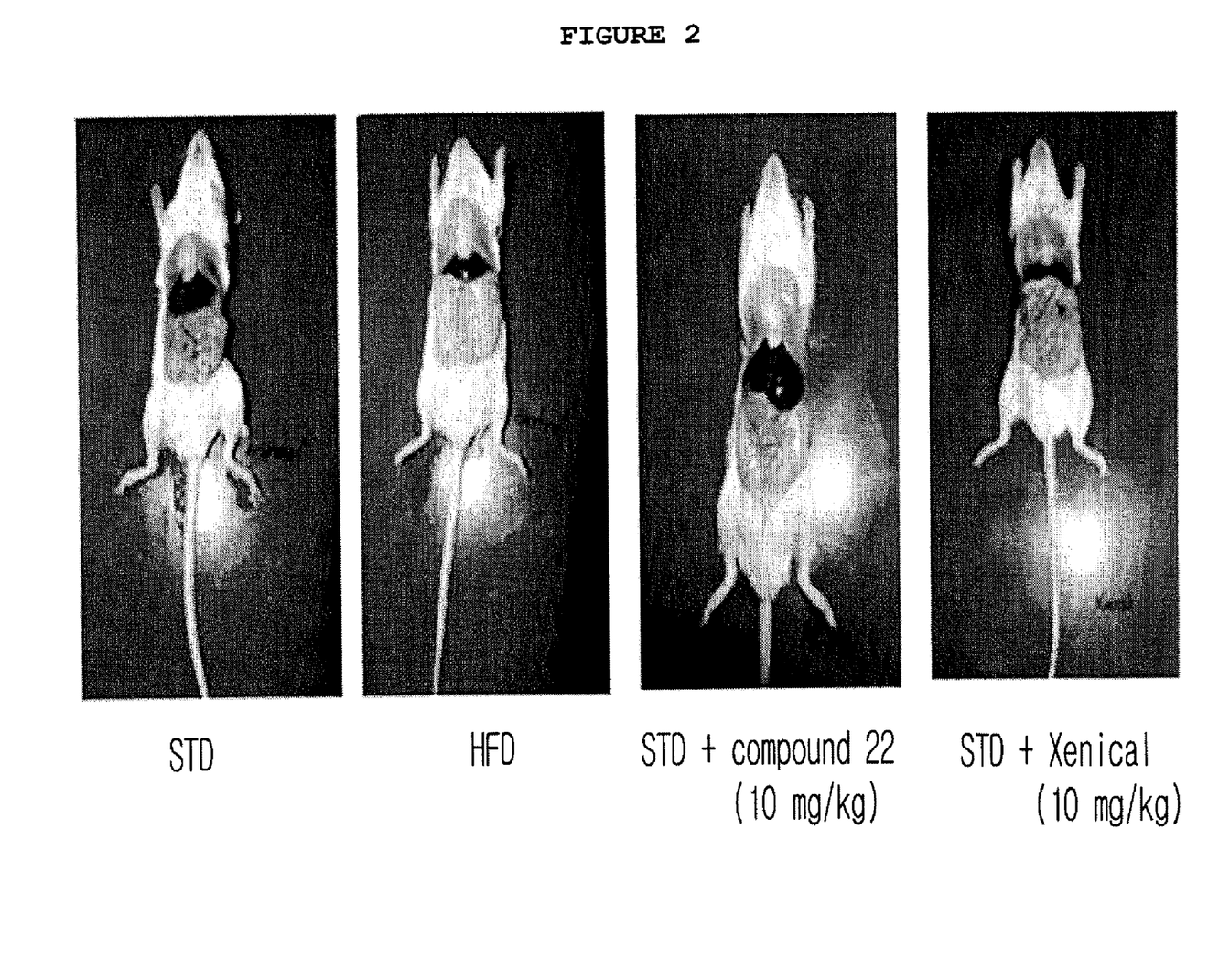
FIG. 2 presents photographs showing anatomized abdomens of mice fed a normal diet or a high-fat diet, with the concurrent oral administration of a benzazole derivative of Chemical Formula 1 or a positive control for 35 days.

On the basis of the control, as seen in FIG. 2, the groups administered with Compound 22 at a dose of 10 mg/kg were significantly decreased in abdominal fat increment compared to the groups fed only with the high-fat diet on the final day. In addition, Compounds 22 and 31 were observed to inhibit body weight gain by 68% and 73% respectively, as understood from the data of Table 5. The inhibition of Xenical, serving as a positive control against body weight gain, was measured to be 88%.

Figure 3:
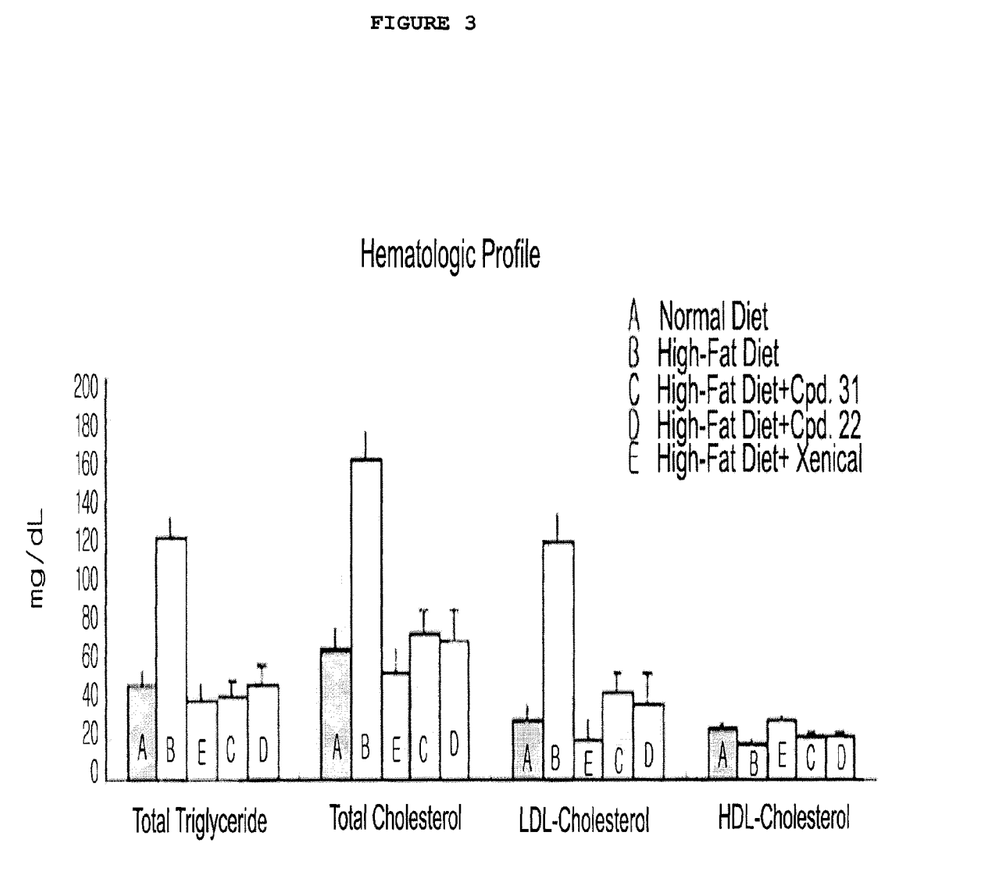
FIG. 3 is a graph showing levels of total triglyceride, total cholesterol, LDL-cholesterol and HDL-cholesterol in the blood of the mice fed with a normal diet or a high-fat diet with the concurrent oral administration of benzazole derivatives of Chemical Formula 1 or a positive control.

Further, the animals administered with Compounds 22 and were analyzed for levels of total triglyceride, total cholesterol, LDL-cholesterol and HDL-cholesterol in blood, and the results are presented in Table 6 and FIG. 3.

TABLE 6

| Group/Diet | Total Triglyceride (mg/dl) | Total Cholesterol (mg/dl) | LDL-Cholesterol (mg/dl) | HDL-Cholesterol (mg/dl) |
|---|---|---|---|---|
| Normal Diet | 46.03 ± 9.89 | 64.72 ± 10.86 | 30.09 ± 8.06 | 26.43 ± 2.69 |
| High-Fat Diet | 120.22 ± 11.21 | 160.00 ± 13.91 | 118.51 ± 14.34 | 17.44 ± 2.15 |
| High-Fat Diet + Cpd. 22 | 48.33 ± 9.83 | 68.89 ± 14.95 | 37.57 ± 15.14 | 21.66 ± 2.16 |
| High-Fat Diet + Cpd. 31 | 41.79 ± 9.26 | 73.19 ± 10.97 | 43.62 ± 10.06 | 21.22 ± 2.19 |
| High-Fat Diet + Xenical | 40.77 ± 6.06 | 53.75 ± 12.35 | 20.45 ± 8.99 | 30.28 ± 1.52 |

(Mean ± SD)

As seen in Table 6 and FIG. 3, the administration of the compounds according to the present invention resulted in decreased levels of total triglyceride, total cholesterol and LDL-cholesterol in the blood to almost normal levels, accompanied with a significant increase in HDL-cholesterol.

Figure 4:
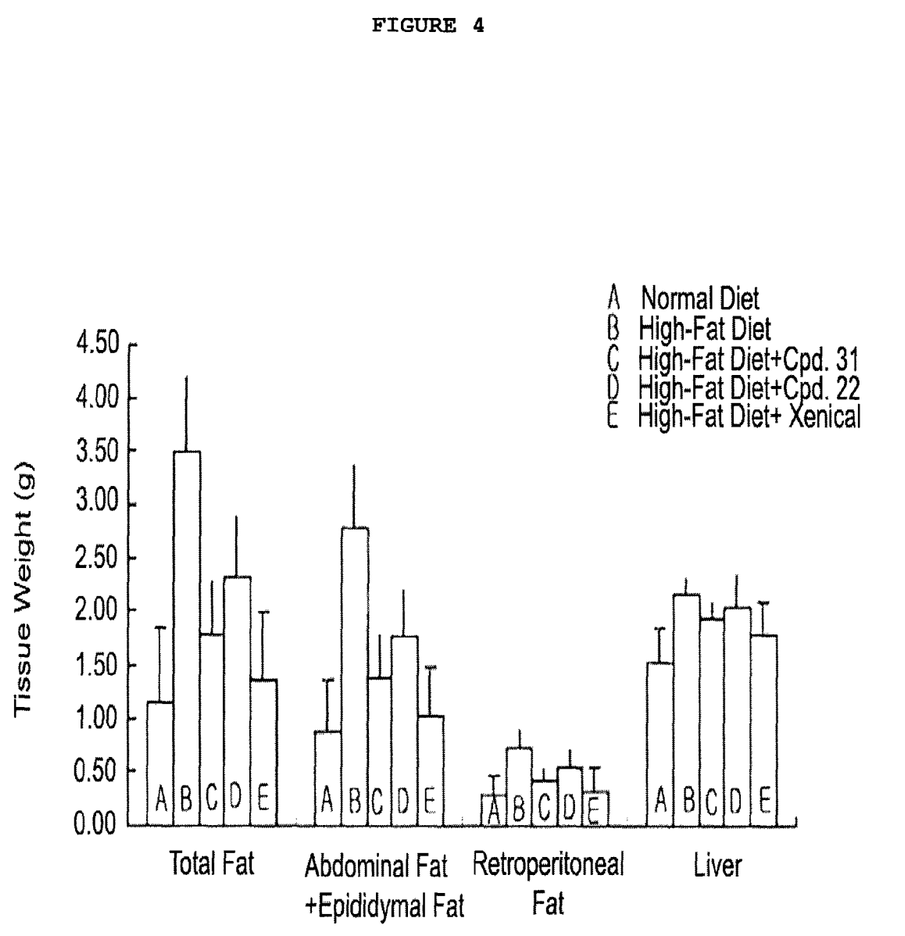
FIG. 4 is a graph showing the weights of total fat, abdominal fat, epididymal fat and retroperitoneal fat in mice fed a normal diet or a high-fat diet with the concurrent oral administration of benzazole derivatives of Chemical Formula 1 or a positive control.

After the completion of administration with Compounds 22 and 31, the animals were measured for weights of total fat, abdominal fat, epididymal fat, and retroperitoneal fat, and the results are presented in Table 7 and FIG. 4.

TABLE 7

| | (Tissue Weight/Body Weight) × 100 | | | |
|---|---|---|---|---|
| Groups/Diets | Total Fat | Abdominal Fat + Epididymal Fat | Retro-peritoneal Fat | Liver |
| Normal Diet | 2.77 ± 1.52 | 2.11 ± 1.09 | 0.66 ± 0.44 | 3.88 ± 0.89 |
| High-Fat Diet | 6.75 ± 1.18 | 5.34 ± 1.09 | 1.41 ± 0.29 | 4.09 ± 0.37 |
| High-Fat Diet + Cpd. 22 | 5.24 ± 0.91 | 3.97 ± 0.72 | 1.24 ± 1.31 | 4.66 ± 0.65 |
| High-Fat Diet + Cpd. 31 | 4.1 ± 1.03 | 3.16 ± 0.84 | 0.94 ± 0.24 | 4.48 ± 0.33 |
| High-Fat Diet + Xenical | 3.20 ± 1.52 | 2.45 ± 1.03 | 0.75 ± 0.50 | 4.31 ± 0.76 |

(Mean ± SD)

As seen in Table 7 and FIG. 4, the administration of the compounds according to the present invention was observed to result in a significant decrease in all of total fat, abdominal fat, epididymal fat and retroperitoneal fat.

Example 4

Assay of Benzazole Derivatives for Acute Toxicity

An assay of the benzazole derivatives of Chemical Formula 1 in accordance with the present invention was performed for acute toxicity on mice (20±5 g, Central Lab. Animal Inc.) and rats (235±10 g, Central Lab. Animal Inc.).

For this, ICR mice and Sprague-Dawley rats were assigned to 4 groups of 10 and orally administered with Compound 22 in doses of 100 and 250 mg/kg for two weeks. Death was observed in none of the four groups, with no apparent symptoms different from the control.

In addition, the compounds of the present invention were orally administered once at a dose of as high as 2,000 mg/kg into mice. In this regard, 7-week-old male SPF ICR mice (Dae Han Biolink Co. Ltd.) were acclimated to a new environment for one week and they, thus 8 weeks old, were divided into two groups of three. The test group was orally administered once with a dose of 2 g/kg of Compound 10 in a 0.5% CMC solution, while the control was administered with a 0.5% CMC (carboxymethyl cellulose) solution alone. They were monitored for death, clinical signs, change in body weight and the like for a couple of weeks. Autopsies were performed to examine the abnormality of organs. The observations are given in Table 8, below.

TABLE 8

| Groups | Mortality | Clinical Signs | Necropsy Findings | Body Weight (g) | | | | |
|---|---|---|---|---|---|---|---|---|
| | | | | Day 0 | Day 1 | Day 3 | Day 7 | Day 14 |
| Test | 0/3 | ND | ND | 35 ± 0.5 | 37 ± 0.5 | 37 ± 0.6 | 39 ± 1.6 | 42 ± 0.8 |
| Control | 0/3 | ND | ND | 33 ± 0.9 | 34 ± 1.2 | 35 ± 1.9 | 36 ± 1.2 | 39 ± 2.1 |

Mortality: No. of Dead/No of Tested
Body Weight: Mean ± SD
ND: Not detected

As seen in Table 8, death was observed in neither of the groups, with no animals observed to behave abnormally or show toxicity syndromes. In addition, both groups were observed to increase in body weight. Upon necropsy, no abnormalities were observed in any thoracic or abdominal organs.

Therefore, the compounds of the present invention exert no oral acute toxicity on mice even when administered once at a dose of up to 2,000 mg/kg.

Taken together, the data obtained in above examples demonstrate that the derivatives of Chemical Formula 1 according to the present invention function to inhibit DGAT within cells to elicit various effects within cells, including the prevention of triglyceride biosynthesis, protection against diet-induced obesity, decreased fat accumulation in adipocytes, and the normalization of blood lipid levels. With the inhibitory activity against DGAT, therefore, the composition comprising the derivatives of Chemical Formula 1 as an active ingredient can be applied to the treatment and prevention of obesity, diabetes, hyperlipidemia and arteriosclerosis.

The invention claimed is:

1. A method for treating a metabolic disorder, comprising administering a therapeutically effective amount of a benzazole derivative represented by the following Chemical Formula 1 or a pharmaceutically acceptable salt thereof to a patient in need of treatment of metabolic disorder, wherein the metabolic disorder is obesity:

<Chemical Formula 1>

(wherein,
$R_1$ is one substituent at position C5 or C6 of a benzoxazole or benzimidazole ring, which is selected from a group consisting of H, $COOR_a$, $CONR_bR_c$ and $SO_2NH_2$, wherein $R_a$ is H or a $C_1$~$C_2$ alkyl group, and
$R_b$ and $R_c$ are independently selected from a group consisting of: a $C_3$~$C_5$ heteroaryl group bearing at least one heteroatom selected from among N, O and S; a $C_3$~$C_5$ heterocyclic group bearing at least one heteroatom selected from among N, O and S; a $C_1$~$C_5$ alkyl group bearing a $C_1$~$C_3$ alkyl-substituted amino group; H; an amino group; and a $C_1$~$C_3$ alkyl group;
$R_2$ is a $C_1$~$C_{10}$ alkyl group, a halogen atom or a nitro group;
$R_3$ is H or a halogen atom; and
X is O or NH).

2. The method according to claim 1, wherein the derivative of Chemical Formula 1 is selected from a group consisting of:
1) 2-(2,4-dichloro-phenoxymethyl)-benzoxazole-5-carboxylic acid methyl ester;
2) 2-(4-adamantan-1-yl-phenoxymethyl)-benzoxazole-5-carboxylic acid methyl ester;
3) 2-(4-adamantan-1-yl-phenoxymethyl)-benzoxazole-6-carboxylic acid methyl ester;
4) 2-(4-adamantan-1-yl-phenoxymethyl)-1H-benzoimidazole-5-carboxylic acid methyl ester;
5) 2-(2,4-dichloro-phenoxymethyl)-benzoxazole-6-carboxylic acid methyl ester;
6) 2-(2,4-dichloro-phenoxymethyl)-1H-benzoimidazole-5-carboxylic acid methyl ester;
7) 2-(2,4-tert-butyl-phenoxymethyl)-benzoxazole-6-carboxylic acid methyl ester;
8) 2-(2,4-tert-butyl-phenoxymethyl)-1H-benzoimidazole-5-carboxylic acid methyl ester;
9) 2-(4-nitro-phenoxymethyl)-1H-benzoimidazole-5-carboxylic acid methyl ester;
10) 2-(2,4-dichloro-phenoxymethyl)-benzoxazole-5-sulfonic acid amide;
11) 2-(2,4-dichloro-phenoxymethyl)-benzoxazole-5-carboxylic acid;
12) 2-(4-adamantan-1-yl-phenoxymethyl)-benzoxazole-5-carboxylic acid;
13) 2-(4-adamantan-1-yl-phenoxymethyl)-benzoxazole-6-carboxylic acid;
14) 2-(4-adamantan-1-yl-phenoxymethyl)-1H-benzoimidazole-5-carboxylic acid;
15) 2-(2,4-dichloro-phenoxymethyl)-benzoxazole-6-carboxylic acid;
16) 2-(2,4-dichloro-phenoxymethyl)-1H-benzoimidazole-5-carboxylic acid;
17) 2-(4-tert-butyl-phenoxymethyl)-benzoxazole-6-carboxylic acid;
18) 2-(4-tert-butyl-phenoxymethyl)-1H-benzoimidazole-5-carboxylic acid;
19) 2-(4-nitro-phenoxymethyl)-1H-benzoimidazole-5-carboxylic acid;
20) 2-(4-adamantan-1-yl-phenoxymethyl)-benzoxazole-5-carboxylic acid amide;
21) 2-(4-adamantan-1-yl-phenoxymethyl)-benzoxazole-5-carboxylic acid dimethylamide;
22) 2-(4-adamantan-1-yl-phenoxymethyl)-benzoxazole-5-carboxylic acid (furan-2-ylmethyl)-amide;
23) 2-(4-adamantan-1-yl-phenoxymethyl)-benzoxazole-5-carboxylic acid (2-dimethylamino-ethyl)-amide;
24) 2-(4-adamantan-1-yl-phenoxymethyl)-benzoxazole-5-carboxylic acid (2-piperidin-1-yl-ethyl)-amide;
25) 2-(4-adamantan-1-yl-phenoxymethyl)-benzoxazole-5-carboxylic acid (3-morpholin-4-yl-propyl)-amide;
26) 2-(2,4-dichloro-phenoxymethyl)-benzoxazole-5-carboxylic acid (furan-2-ylmethyl)-amide;
27) 2-(4-adamantan-1-yl-phenoxymethyl)-benzoxazole-6-carboxylic acid (furan-2-ylmethyl)-amide;
28) 2-(4-dichloro-phenoxymethyl)-benzoxazole-6-carboxylic acid (furan-2-ylmethyl)-amide;
29) 2-(4-adamantan-1-yl-phenoxymethyl)-3H-benzoimidazole-5-carboxylic acid amide;
30) 2-(4-adamantan-1-yl-phenoxymethyl)-3H-benzoimidazole-5-carboxylic acid dimethylamide;
31) 2-(4-adamantan-1-yl-phenoxymethyl)-1H-benzoimidazole-5-carboxylic acid (furan-2-ylmethyl)-amide;
32) 2-(4-adamantan-1-yl-phenoxymethyl)-1H-benzoimidazole-5-carboxylic acid (2-dimethylamino-ethyl)-amide;
33) 2-(4-adamantan-1-yl-phenoxymethyl)-1H-benzoimidazole-5-carboxylic acid (3-imidazol-1-yl-propyl)-amide;
34) 2-(2,4-dichloro-phenoxymethyl)-1H-benzoimidazole-5-carboxylic acid hydrazide; and
35) 2-(2,4-dichloro-phenoxymethyl)-3H-benzoimidazole-5-carboxylic acid (furan-2-ylmethyl)-amide.

3. The method of claim 1, wherein the benzazole derivative is administered orally.

4. The method of claim 3, wherein administration of the benzazole derivative inhibits diacylglycerol acyltransferase (DGAT) and triglyceride biosynthesis.

5. The method of claim 1, wherein one to three doses of the benzazole derivative is administered to the patient per day, wherein each dose comprises between 1 to 250 mg/kg.

* * * * *